United States Patent
Kim et al.

(10) Patent No.: US 9,271,694 B2
(45) Date of Patent: Mar. 1, 2016

(54) SYSTEM AND METHOD OF SIMPLIFYING A DIRECT CONTROL SCHEME FOR A DETECTOR

(71) Applicant: General Electric Company, Schenectady, NY (US)

(72) Inventors: Chang L. Kim, Waukesha, WI (US); David L. McDaniel, Waukesha, WI (US); Vi-Hoa Tran, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 210 days.

(21) Appl. No.: 14/132,164

(22) Filed: Dec. 18, 2013

(65) Prior Publication Data

US 2015/0168567 A1    Jun. 18, 2015

(51) Int. Cl.
| | |
|---|---|
| *G01T 1/24* | (2006.01) |
| *A61B 6/00* | (2006.01) |
| *A61B 6/03* | (2006.01) |
| *G01T 1/20* | (2006.01) |
| *G01T 1/208* | (2006.01) |

(52) U.S. Cl.
CPC ............... *A61B 6/585* (2013.01); *A61B 6/037* (2013.01); *G01T 1/208* (2013.01); *G01T 1/2018* (2013.01); *G01T 1/248* (2013.01)

(58) Field of Classification Search
CPC ........ A61B 6/585; A61B 6/037; G01T 1/248; G01T 1/208; G01T 1/2018
USPC .................. 250/370.11, 371, 252.1
See application file for complete search history.

(56) References Cited

U.S. PATENT DOCUMENTS

| | | | |
|---|---|---|---|
| 7,439,509 B1 * | 10/2008 | Grazioso ............... | G01T 1/2018 250/338.4 |
| 7,652,257 B2 * | 1/2010 | Li ........................ | G01T 1/2018 250/370.01 |
| 8,269,177 B2 | 9/2012 | Kim et al. | |
| 8,467,644 B1 | 6/2013 | Kim et al. | |
| 9,121,766 B2 * | 9/2015 | Mazzillo ................... | G01J 1/46 |
| 2006/0175529 A1 * | 8/2006 | Harmon ................ | B82Y 20/00 250/207 |
| 2010/0219347 A1 * | 9/2010 | Schulz .................. | G01T 1/1603 250/363.04 |
| 2010/0316184 A1 * | 12/2010 | Iwanczyk .............. | A61B 6/032 378/19 |
| 2011/0192982 A1 * | 8/2011 | Henseler ............... | G01T 1/2985 250/362 |
| 2011/0215248 A1 * | 9/2011 | Lewellen .............. | G01T 1/1647 250/363.03 |
| 2011/0248175 A1 * | 10/2011 | Frach .................... | G01T 1/2018 250/363.03 |
| 2012/0068050 A1 * | 3/2012 | Mazzillo ................... | G01J 1/46 250/208.1 |
| 2012/0132814 A1 * | 5/2012 | Weinberg ............. | G01V 5/0075 250/362 |
| 2013/0249035 A1 * | 9/2013 | Hedler .................. | G01T 1/2018 257/432 |
| 2013/0313414 A1 * | 11/2013 | Pavlov ................. | H01L 31/0224 250/214.1 |
| 2014/0021330 A1 * | 1/2014 | Russo ................ | G01N 21/6454 250/206 |

(Continued)

FOREIGN PATENT DOCUMENTS

| | | | | |
|---|---|---|---|---|
| IT | MI2013A000019 | * | 9/2013 | ............ G01S 17/026 |
| JP | 2014-241543 | * | 12/2014 | ................ G01T 1/17 |
| JP | 2015-065531 | * | 3/2015 | ................ G01T 1/17 |

*Primary Examiner* — David Porta
*Assistant Examiner* — Gisselle Gutierrez
(74) *Attorney, Agent, or Firm* — Dean D. Small; The Small Patent Law Group, LLC (57) ABSTRACT

An imaging system includes a first silicon photomultiplier (SiPM) comprising an array of microcells. Each microcell is an avalanche photodiode (APD) operated in a Geiger mode, a first area of the first SiPM, comprising at least one of the microcells, is electrically isolated from all other microcells, and a signal from the first area, resulting from at least one photon pulse, is used to determine a gain of the first SiPM.

19 Claims, 7 Drawing Sheets

(56) References Cited

U.S. PATENT DOCUMENTS

| | | | |
|---|---|---|---|
| 2014/0191114 A1* | 7/2014 | Russo | G01S 17/08 250/208.2 |
| 2014/0339398 A1* | 11/2014 | Mazzillo | H01L 27/1446 250/208.2 |
| 2014/0367576 A1* | 12/2014 | Sasaki | G01T 1/1647 250/366 |
| 2014/0367577 A1* | 12/2014 | Badawi | A61B 6/037 250/366 |
| 2015/0001403 A1* | 1/2015 | Kim | G01T 1/1642 250/363.03 |
| 2015/0085985 A1* | 3/2015 | Funaki | H03M 1/145 378/98 |
| 2015/0177394 A1* | 6/2015 | Dolinsky | G01T 1/208 250/252.1 |

* cited by examiner

SYSTEM AND METHOD OF SIMPLIFYING A DIRECT CONTROL SCHEME FOR A DETECTOR

BACKGROUND

The subject matter disclosed herein relates to detection systems for use in imaging systems, such as X-ray based and nuclear medicine imaging systems.

Diagnostic imaging technologies allow images of the internal structures of a patient to be obtained and may provide information about the function and integrity of the patient's internal structures. Diagnostic imaging systems may operate based on various physical principles, including the emission or transmission of radiation from the patient tissues. For example, X-ray based imaging systems may direct X-rays at a patient from some emission source toward a detector system disposed opposite the source across an imaged volume. Attenuation of the X-rays as they pass through the volume, and through any materials or tissues placed between the source and detector, may be determined and used to non-invasively form images of the interior regions of an imaged patient or object. Such attenuation information may be obtained at various angular displacements to generate depth information coincident with the attenuation information.

In addition, single photon emission computed tomography (SPECT) and positron emission tomography (PET) may utilize a radiopharmaceutical that is administered to a patient and whose breakdown results in the emission of gamma rays from locations within the patient's body. The radiopharmaceutical is typically selected so as to be preferentially or differentially distributed in the body based on the physiological or biochemical processes in the body. For example, a radiopharmaceutical may be selected that is preferentially processed or taken up by tumor tissue. In such an example, the radiopharmaceutical will typically be disposed in greater concentrations around tumor tissue within the patient.

In the context of PET imaging, the radiopharmaceutical typically breaks down or decays within the patient, releasing a positron which annihilates when encountering an electron and produces a pair of gamma rays moving in opposite directions in the process. In SPECT imaging, a single gamma ray is generated when the radiopharmaceutical breaks down or decays within the patient. These gamma rays interact with detection mechanisms within the respective PET or SPECT scanner, which allow the decay events to be localized, thereby providing a view of where the radiopharmaceutical is distributed throughout the patient. In this manner, a caregiver can visualize where in the patient the radiopharmaceutical is disproportionately distributed and may thereby identify where physiological structures and/or biochemical processes of diagnostic significance are located within the patient.

In the above examples of imaging technologies, a detector is employed which converts incident radiation to useful electrical signals that can be used in image formation. Certain such detector technologies employ a silicon photomultiplier (SiPM), which is a single anode device containing a number of microcells, and which are useful for detecting optical signals generated in a scintillator in response to incident radiation. One issue that may arise is, in certain detector technologies where SiPMs are employed, the gain of the respective detection elements may be temperature dependent. Such temperature related variation in gain may be problematic in imaging applications. In addition, the SiPM may show temperature sensitivity due to doping variations, or the SiPM may age due to radiation exposure or other affects that can cause gain drift. Even though temperature is known to be the main cause of SiPM gain drift, those other factors can cause uncertainty or error in knowing the gain of the SiPM, therefore preventing the ability to accurately measure gamma ray energy.

To address these affects, certain conventional approaches to monitor the temperature include using sensors, such as thermistors, to compensate the bias voltage (Vbias) to maintain constant over-voltage and account for overall gain drift. However, these conventional approaches typically employ the temperature sensors separate from the SiPM, and are placed in proximity to the SiPM. As a result, the temperature sensors do not measure the actual temperature of the SiPM and so drift in gain is typically not accounted for. Even thermistors can be embedded in a SiPM to be more representative of SiPM temperature, it may not account for the gain error caused by the other factors mentioned above. Thus, there is a need to improve gain compensation in detectors for imaging systems by measuring the gain directly.

BRIEF DESCRIPTION

Embodiments are directed toward an apparatus and method to determine a gain for a detector.

According to one aspect, an imaging system includes a first silicon photomultiplier (SiPM) comprising an array of microcells. Each microcell is an avalanche photodiode (APD) operated in a Geiger mode, a first area of the first SiPM, comprising at least one of the microcells, is electrically isolated from all other microcells, and a signal from the first area, resulting from at least one photon pulse, is used to determine a gain of the first SiPM.

According to another aspect, a method of measuring a gain includes receiving a signal from a first area of a first silicon photomultiplier (SiPM), wherein the first area comprises at least one microcell that is part of but isolated from an array of microcells, and wherein each microcell in the array is a Geiger mode avalanche photodiode (APD), and measuring the gain of the first SiPM using the signal that results from at least one photon pulse that emanates from a scintillator that is coupled to the first SiPM, or at least one photon pulse that is originated from dark count.

According to yet another aspect, a system for calibrating a detector includes a first silicon photomultiplier (SiPM) comprising a first array of microcells, each of which is an avalanche photodiode (APD) operated in a Geiger mode, a first area of the first array, comprising at least one of the microcells electrically isolated from all other microcells of the first array, a signal from the first area, resulting from at least one photon pulse, is used to determine a gain of the first SiPM, and a scintillator optically coupled to the first SiPM, wherein gamma rays emitted from a patient positioned in the imaging system pass to the scintillator and generate photons that pass to the first SiPM.

Various other features and advantages will be made apparent from the following detailed description and the drawings.

DETAILED DESCRIPTION

The operating environment of disclosed examples is described with respect to a PET system, but it is contemplated that the disclosed subject matter may also be useful in other imaging contexts, such as in a SPECT imaging system or in an X-ray based imaging system, such as computed tomography, bone densitometry system. Indeed, the present approach may be employed in conjunction with any nuclear radiation detector that is based on the use of scintillators with a silicon photomultiplier (SiPM) readout.

Figure 1:
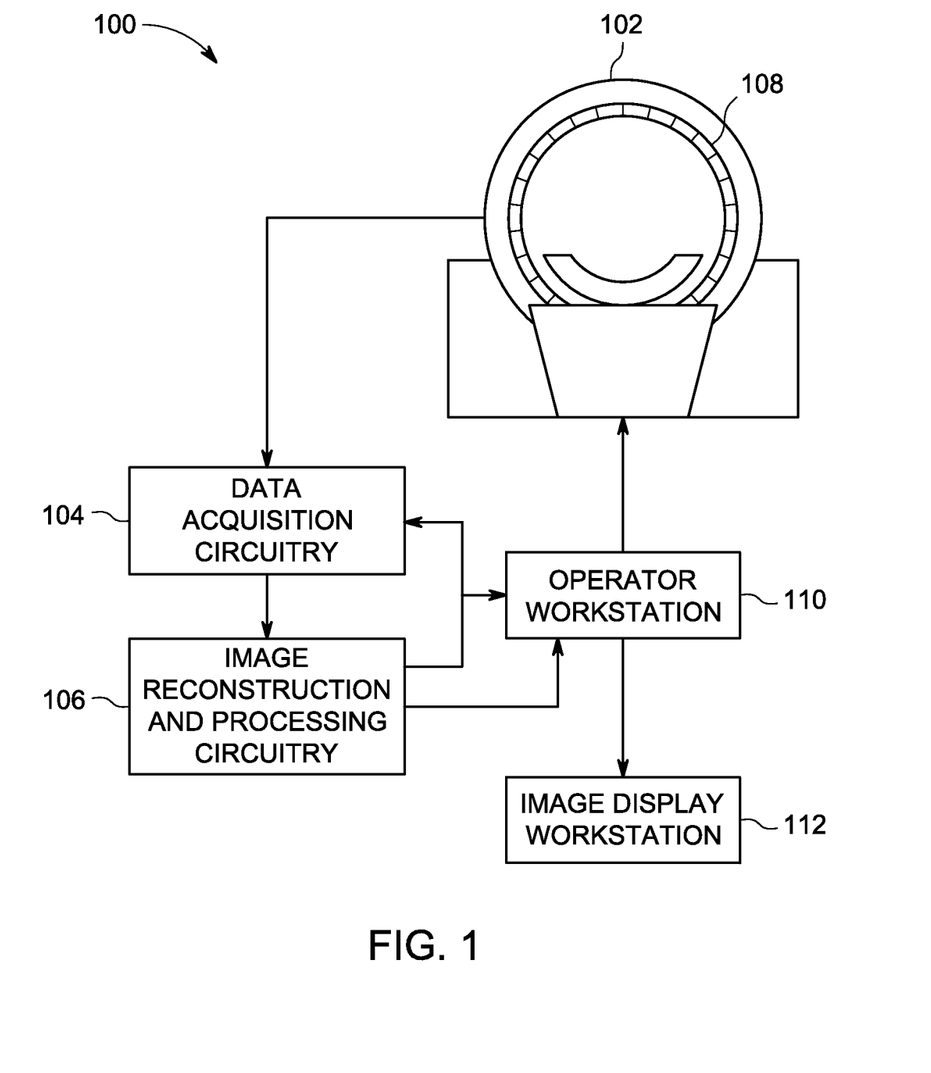
FIG. 1 is a diagrammatical representation of a PET imaging system in accordance with aspects of the present disclosure.

FIG. 1 depicts a PET system 100 operating in accordance with aspects of the present disclosure. Such a PET system 100 may be used in isolation or in conjunction with another imaging modality, such as a CT or MRI imaging system. PET system 100 includes a detector assembly 102, data acquisition circuitry 104, and image reconstruction and processing circuitry 106. Detector assembly 102 of PET system 100 typically includes a number of detector modules (generally designated by reference numeral 108) arranged about the imaging volume. Detector assembly 102, via modules 108, is configured to generate signals in response to gamma rays generated by positron annihilation events and emitted from a subject within an imaged volume. In certain implementations, detector assembly 102 can include scintillators and photon detection electronics. Detector assembly 102 may be of any suitable construction and configuration for acquiring PET data. For example, as in the depicted example, detector assembly 102 can be configured as a full or partial ring.

In certain implementations, gamma rays may be converted, such as in a scintillator of detector assembly 102 or detector modules 108, to lower energy photons that in turn may be detected and converted in the detector modules 108 to electrical signals, which can be conditioned and processed to output digital signals. These output signals can be used to match pairs of gamma ray detections as potential coincidence events. That is, in such a PET implementation, when two gamma rays strike opposing detectors it may be determined that a positron annihilation occurred on a line connecting the two impact locations (absent the effects of interactions of random and scatter detections). In a SPECT implementation, as another example, line of flight information may instead be inferred based at least in part on the collimation associated with the detector assembly. The collected data can be sorted and integrated and used in subsequent processing such as by image reconstruction and processing circuitry 106.

Thus, in operation, detector acquisition circuitry 104 is used to read out signals from detector modules 108 of detector assembly 102, where the signals are generated in response to gamma rays emitted within the imaged volume. The signals acquired by data acquisition circuitry 104 are provided to the image reconstruction and processing circuitry 106. Image reconstruction and processing circuitry 106 generates an image based on the derived gamma ray emission locations. An operator workstation 110 is utilized by a system operator to provide control instructions to some or all of the described components and for configuring the various operating parameters that aid in data acquisition and image generation. Operating workstation 110 may also display the generated image. Alternatively, the generated image may be displayed at a remote viewing workstation, such as an image display workstation 112.

It should be appreciated that, to facilitate explanation and discussion of the operation of PET system 100, data acquisition circuitry 104 and the image reconstruction and processing circuitry 106 have been shown separately in FIG. 1 from other illustrated components (e.g., detector assembly 102, operator workstation 110, and image display workstation 112). However, it is contemplated that, in certain implementations, some or all of these circuitries may be provided as part of detector assembly 102, operator workstation 110, and/or image display workstation 112. For example, the hardware, software, and/or firmware executed on or provided as part of data acquisition circuitry 104, whether provided as part of detector assembly 102, operator workstation 110, and/or image display workstation 112, may be used to perform various detector readout and/or control actions described herein. In certain implementations data acquisition circuitry 104 may include specially configured or programmed hardware, memory, or processors (e.g., application-specific integrated circuits (ASICs)) for performing gain compensation as discussed herein. Similarly, certain of these compensation functions may be performed using one or more general or special purpose processors and stored code or algorithms configured to execute on such processors. Likewise, a combination of special purpose hardware and/or circuitry may be used in conjunction with one or more processors configured to execute stored code to implement the gain compensation steps discussed herein.

The detector technology in one implementation of a system such as that depicted in FIG. 1 will be discussed in greater detail. In particular, a PET or SPECT system may utilize arrays of solid-state silicon photomultiplier (SiPM) devices as part of the gamma ray detection mechanism, e.g., as part of detector modules 108. Such SiPM devices may take the form, in certain implementations, as an array of microcells of avalanche photodiodes (APD) operated in Geiger mode for detecting impinging photons. In general, SiPM devices used for photon detection can provide information about certain parameters, such as the time of the impingement event, the energy associated with the event, and the position of the event within the detector, as examples. These parameters can be determined through processing algorithms applied to the signals generated by the SiPM.

Figure 2:
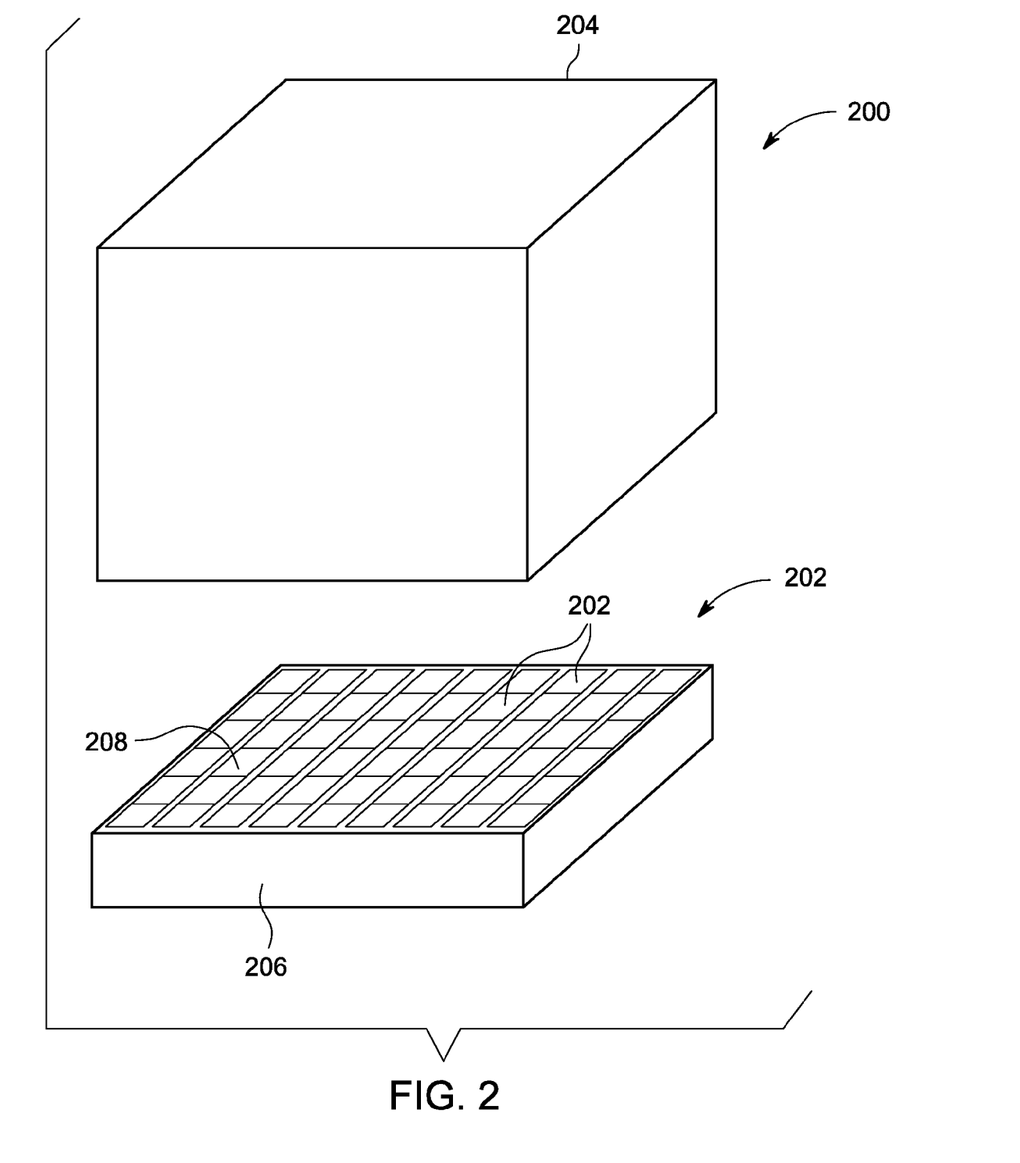
FIG. 2 depicts a perspective view of a detector SiPM, in accordance with aspects of the present disclosure.

Referring to FIG. 2, an exemplary SiPM detector 200 is illustrated that incorporates elements of the present disclosure. A SiPM device 202 is formed using a semiconductor material such as silicon and is a single anode device, and each SiPM device 202 comprises a plurality of microcells 208 that may range in size from, as examples, 20 to 200 microns. A scintillator 204 is positioned on top of and optically coupled to microcells 208. Each microcell 208 is an avalanche photodiode (APD) that is a single photon sensitive device built as an array on a common silicon substrate 206, and the APDs are combined to form a macroscopic unit. Each microcell 208 amplifies single optical photon arrivals from the scintillator 204 into an output signal. Typically, each SiPM device 202 contains a large number of microcells 208 (e.g., between 25 to 2,500 APDs per mm$^2$), and each of the microcells 208 operates as an individual Geiger-mode APD. In this mode of operation, an optical photon generated in scintillator 204 traverses scintillator 204 to one of the microcells 208, and an electron generated by the absorption of the optical photon in microcell 208 initiates an avalanche breakdown that is confined to microcell 208.

SiPMs incorporate an array of APD microcells operating in Geiger mode. A breakdown voltage ($V_{br}$) of the microcell depends on its temperature. For example, a typical temperature coefficient is about +30 to +60 mV/° C. for known APD structures. The SiPM works above the breakdown voltage in Geiger mode and the associated gain is proportional to an over-voltage ($V_{ov}=V_{op}-V_{br}$), where $V_{op}$ is an operating voltage applied from a power supplier As a result, the gain at a given microcell depends at least in part on temperature due to the dependence of breakdown voltage on temperature. For example, a gain temperature coefficient may be between about –30 to –60 mV/$V_{ov}$. For a typical over-voltage of 2 V, this may translate to a gain temperature coefficient of approximately –1.5% to –3%/° C., as an example. As such, the respective gain corresponds to the decrease in signal seen for each event, and a lower gain corresponds to poor light amplification. However, knowledge of the amount of gain present in the SiPM at a given time may be necessary to determine the actual magnitude of the radiation incident on the detector. Variations in gain due to temperature effects, device to device difference in gain temperature coefficient due to doping variations, aging and the like, may lead to uncertainty with respect to the magnitude of the actual underlying event being measured and hard to be corrected with just temperature measurement.

Thus, in operation, SiPM device 202 remains in a steady state until a free carrier such as an incident photon enters the depletion zone of an APD, such as microcell 208, from scintillator 204. The photon generates an electron/hole pair, which acts as a charge carrier that is accelerated by the electric field set by the bias voltage provided, releasing other carriers by impact ionization. With the bias voltage above breakdown, the liberated carriers acquire enough energy to ionize more carriers in turn, resulting in triggering a self-sustaining avalanche. The avalanche is then quenched by suitable external circuitry, which includes a large load resistance for the current and hence reduces the bias voltage on the SiPM to below the breakdown voltage. This stops the current flow in the detector and turns off the avalanche and allows the detector to recover and be able to detect another photon. Depending on the device structure, recovery times ranging from 3 ns to 50 ns can be observed.

Each microcell 208 functions independently of the others to detect photons. In one example, the microcells 208 are electrically connected in parallel to yield an integrated charge over an area over which the signals are being aggregated. The summed discharge currents of the microcells 208 are indicative of the incidence of radiation over a given area, such as that of SiPM device 202, and the output provides magnitude information regarding the incident photon flux over the area for which signals are being aggregated.

Incidentally, it should be appreciated that, to facilitate explanation and discussion of the operation of detector modules 108, SiPM device 202 has been described as containing a single area over which the signals are aggregated (a single anode), however in at least some implementations, the detector module may use monolithic silicon devices which contain multiple SiPMs 202 which have a common cathode and separated anodes 34.

Figure 3:
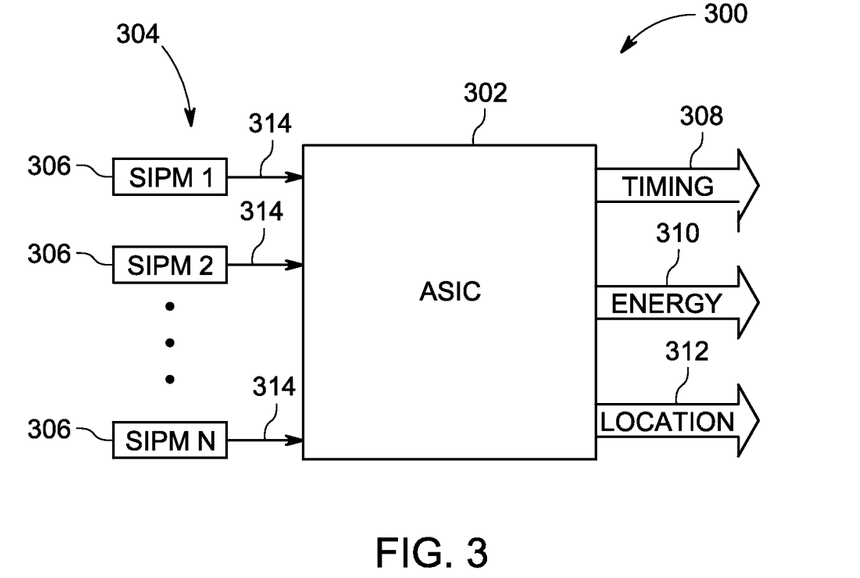
FIG. 3 is a block diagram that represents, in one example, a multichannel readout application-specific integrated circuit (ASIC) interfaced with an array of SiPMs.

Referring to FIG. 3, a block diagram 300 is shown that represents, in one example, a multichannel readout front-end application-specific integrated circuit (ASIC) 302 interfaced with an array 304 of SiPMs 306 (such as SiPM device 202 of FIG. 2) in a PET (or SPECT) system. ASIC 302 may be provided as part of data acquisition circuitry 104 of FIG. 1, and may be configured to provide information on the timing 308, energy 310, and location 312 of events in each SiPM 306 to a processing system (e.g., processing circuitry 106), as well as the ability to bias each SiPM 306. Thus, block diagram 300 represents a PET data acquisition system, such as data acquisition circuitry 104 used with detector array 108 of PET system 100 of FIG. 1.

Block diagram 300 shows array 304 of SiPMs 306 coupled to ASIC 302 as part of detector modules 108 and/or data acquisition circuitry 104. Light generated in scintillator 204 in response to a gamma ray interaction is detected by one of the SiPMs 306 and amplified. In this example, each SiPM 306 includes an anode output 314 in electrical communication with ASIC 302. That is, outputs 314 of SiPMs 306 are the inputs to ASIC 302. ASIC 302 in turn provides timing signals 308, energy signals 310, and/or location or position signals 312 as outputs, as examples. Each of the signals 314 output to ASIC 302 corresponds to information obtained from the respective SiPMs 306, which is then processed by ASIC 302. In one example, data acquisition system 104 can include eighteen (18) SiPMs 306. However, in other implementations, other quantities of SiPMs 306 may be present within data acquisition system 104.

Figure 4:
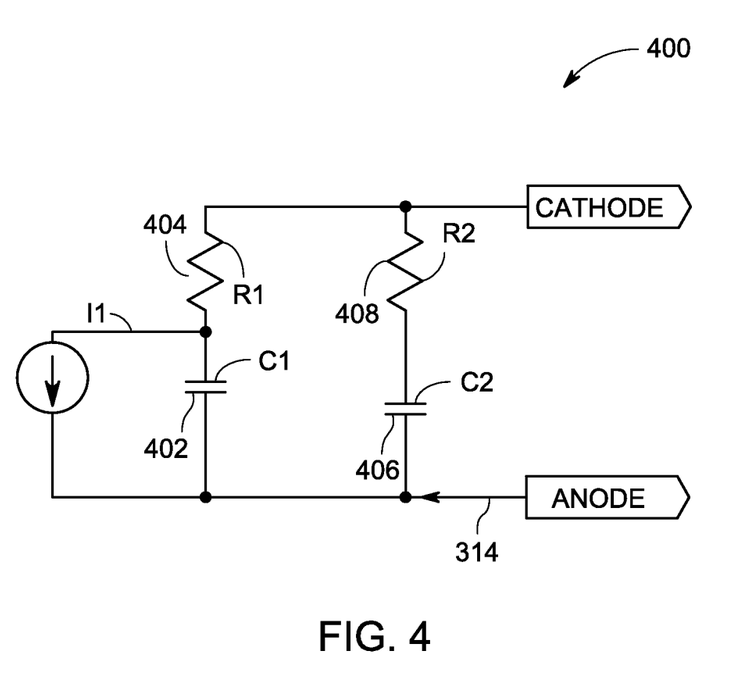
FIG. 4 depicts a simplified electrical model of one example of a SiPM circuit, in accordance with aspects of the present disclosure.

Referring to FIG. 4, an example of an electrical circuit 400 corresponding to a SPICE model of SiPM 306 is depicted. In this example, output 314 from a common anode of each SiPM 306, which as noted with respect to FIG. 3, corresponds to inputs for ASIC 302. C1 402 and R1 404 are respectively the capacitor and quenching resistor for one microcell which detects one photon of the current I1. C2 406 and R2 408 are the equivalent capacitor and resistor of the rest of microcells in a SiPM 306. This depicts how one microcell works independently with respect to the rest of microcells.

In addition to the signal generated in each SiPM from photon impingement in the SiPM, electron/hole pairs can also be generated in the depletion region by thermal generation of carriers or by bulk diffusion of minority carriers from the quasi-neutral region. The thermal generation of electron/hole pairs and thermal bulk diffusion represents the characteristic noise of this type of detectors and, being undistinguishable from the real signal, sets a limit for the ultimate sensitivity of these devices. In the absence of light, the electrical effect of these mechanisms is referred to as dark count rate and determines the number of noise counts generated in the detector per second per unit area. So, the total dark count rate of a SiPM increases with its size. The larger the size of a SiPM become, the more dark count is going to be generated. While a large anode size is an important enabler of PET detector design based on SiPMs by reducing its readout electronics and cost, it generates more dark counts that prevents from measuring dark counts directly. That is, since a large area, such as a 4 mm by 6 mm anode of each SiPM 306, excess dark counts prevent seeing single photon signals due to pileup of many single photon pulses.

As such, according referring to FIGS. 5-8, exemplary embodiments of a detector are illustrated which may be implemented in an imaging system such as system 100, for obtaining a gain (or referred to also as calibrating) of SiPMs without depending on its size or total dark count of a SiPM, by the isolation of a small area within a SiPM. The illustrated embodiments show one or more SiPMs, each including an array of microcells, wherein each microcell is an avalanche photodiode (APD) operated in a Geiger mode. The SiPMs include an area that includes at least one of the microcells electrically isolated from all other microcells, and a signal from the first area, resulting from at least one photon pulse, is used to determine a gain of the first SiPM. In each example and as described with respect to FIG. 2, a scintillator is optically coupled to the SiPMs. Gamma rays emitted from, for instance, a patient positioned in imaging system 100 pass to the scintillator and generate photons that pass to the SiPM. However, the isolation mechanism of a small area in a SiPM requires a separate readout electronics that doubles the amount of channels. The below examples show how to reduce this extra readout channel with a multiplexer or switching mechanism when dealing with multiple SiPM devices.

The illustrated examples include at least one multiplexer electrically coupled to the area of the first SiPM that is electrically isolated from the array of microcells. The multiplexer(s) are configured to receive the signal from the isolated area of each SiPM and selectively pass the signal to a high gain amplifier. This reduces the number of readout channels from N SiPM channels to 1 channel. This is possible since gain calibration can be done in a regular interval, like 1 µs to 30 sec as an example, and does not have to run continuously for each SiPM due to thermal inertia. The examples also include an application-specific integrated circuit (ASIC) electrically coupled to the SiPMs, wherein imaging signals from the SiPMs pass to the ASIC and are converted to digitized imaging data in the ASIC. Since these imaging signals are readout continuously, they are not multiplexed.

Figure 5:
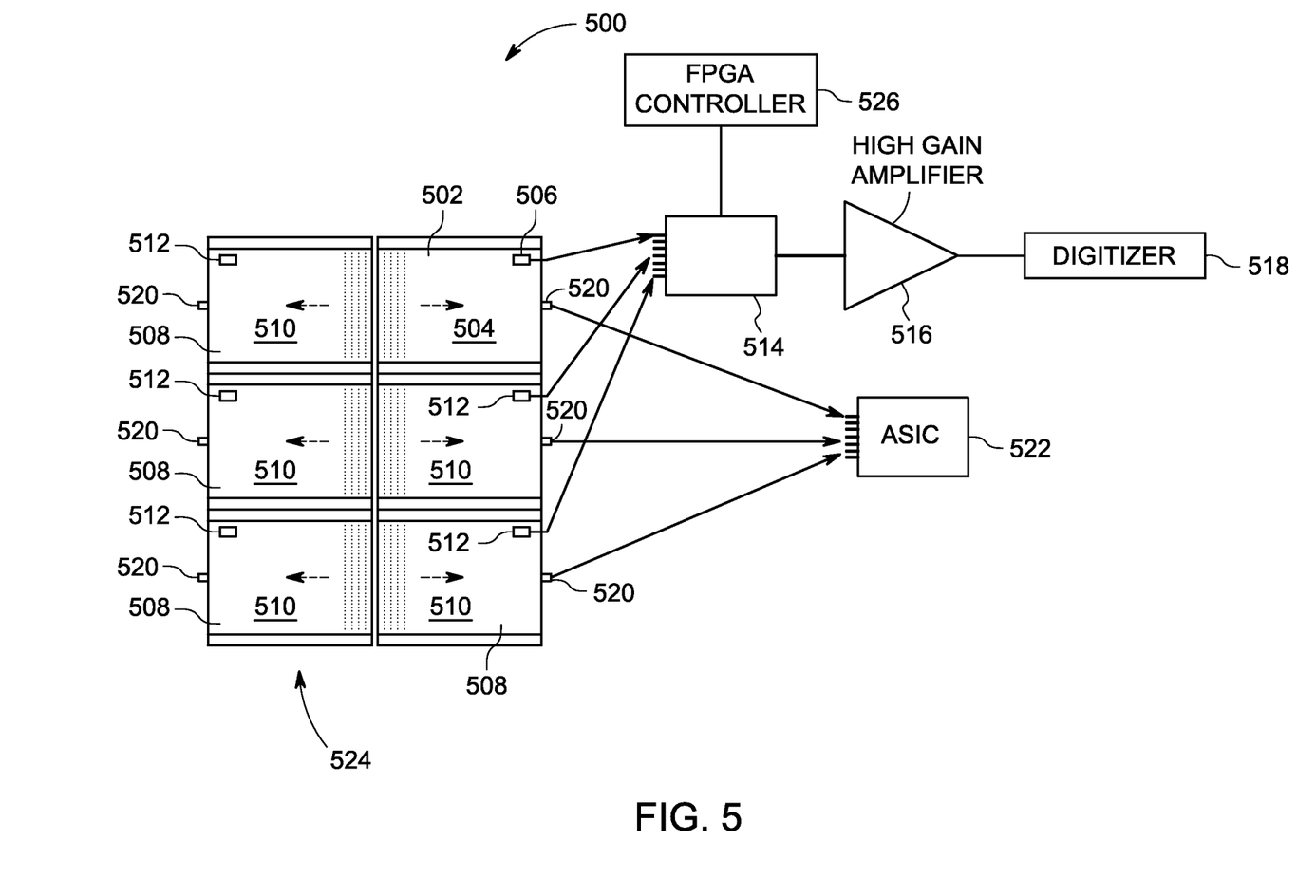
FIG. 5 illustrates a block diagram of SiPMs having areas for gain determination, and a multiplexer and gain amplifier located apart from the SiPMs.

For example, referring to FIG. 5, detector 500 includes an SiPM 502 that includes an array 504 of microcells that are APDs operated in Geiger mode. An area 506 of one or more microcells is electrically isolated from all others of array 504. Other SiPMs 508 include respective arrays 510 of microcells, as well, and each includes a respective isolated area 512 of one or more microcells. Areas 506, 512 are electrically coupled to a multiplexer (MUX) 514 that is controlled by a FPGA controller 526, which is in turn coupled to a high-gain amplifier 516 and a digitizer 518. Anode outputs 520 are common anodes to each respective array 504, 510 of microcells, and each anode output 520 is electrically coupled to an ASIC 522 (and SiPMs 524 are also coupled to multiplexer 514 and ASIC 522, though not shown, but may be coupled to another multiplexer and ASIC, in another example). As shown, multiplexer 514 is positioned apart from SiPMs 502, 508, and positioned to receive a signal from areas 506, 512 of the SiPMs 502, 508 to determine a gain of each SiPM 502, 508, and ASIC 522 is positioned apart from SiPMs 502, 508, as well.

In operation, multiplexer 514 separately accesses each respective area 506, 512, such that a single photon gain measurement may be made for each SiPM 502, 508, which is separately read out to amplifier 516 and digitized 518. Because one multiplexer 514 and one amplifier 516 do not add significant cost or power requirements, the illustrated example therefore can be implemented on a readout board (not shown) if such space is available thereon. This was possible since the gain calibration can be done in a regular interval. In this embodiment, the multiplex can be embedded inside each SiPM since CMOS based SiPM can have electronics on it.

Figure 6:
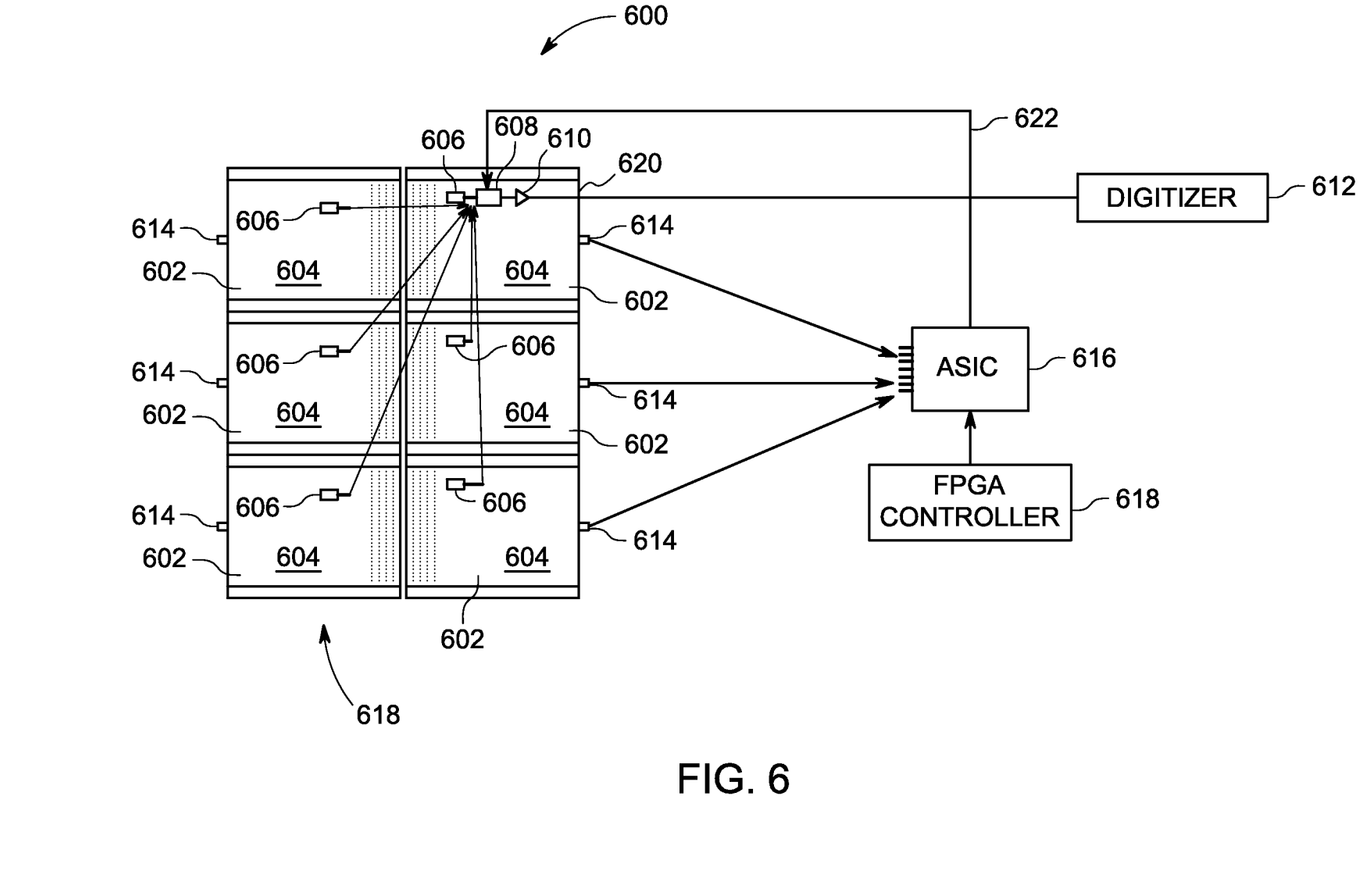
FIG. 6 illustrates a block diagram of SiPMs having areas for gain determination, and a multiplexer and gain amplifier located as part of the SiPMs.

According to another example, FIG. 6 illustrates a detector 600 having SiPMs 602 that include arrays 604 of microcells that are APDs operated in Geiger mode. Each SiPM 602 includes an area 606 of one or more microcells electrically isolated from all others of arrays 604. Areas 606 are electrically coupled to a multiplexer (MUX) 608, which is in turn coupled to a high-gain amplifier 610 and a digitizer 612. The high gain amplifier can be placed externally like a digitizer shown in the FIG. 6. Anode outputs 614 are common anodes to each respective array 604 of microcells, and each anode output 614 is electrically coupled to an ASIC 616 (and SiPMs 618 are also coupled to ASIC 616, though not shown, but may be coupled to another ASIC, in another example). An FPGA controller 618 controls ASIC 616 and MUX 608. As shown, multiplexer 608 and high-gain amplifier 610 are positioned as part of one of the SiPMs 620 in a monolithic SiPM device, and positioned to receive a signal from areas 606 of the SiPMs 602 to determine a gain of each SiPM 602. ASIC 616 is positioned apart from SiPMs 602. Thus, FIG. 6 illustrates an example wherein multiplexer 608 is positioned as part of one of the SiPMs 620, and positioned to receive signals from area 606 to determine the gain of the respective SiPMs. As such, in an example where the SiPM is a CMOS, as an example, electronic circuitry is directly on the SiPM device, and the multiplexing and/or amplifier function can be moved into the SiPM to reduce electronics parts, and controlled via a multiplexing control signal 622. Exemplary in FIGS. 5 and 6 shows gain compensation can be done in parallel with patient data collection.

Figure 7:
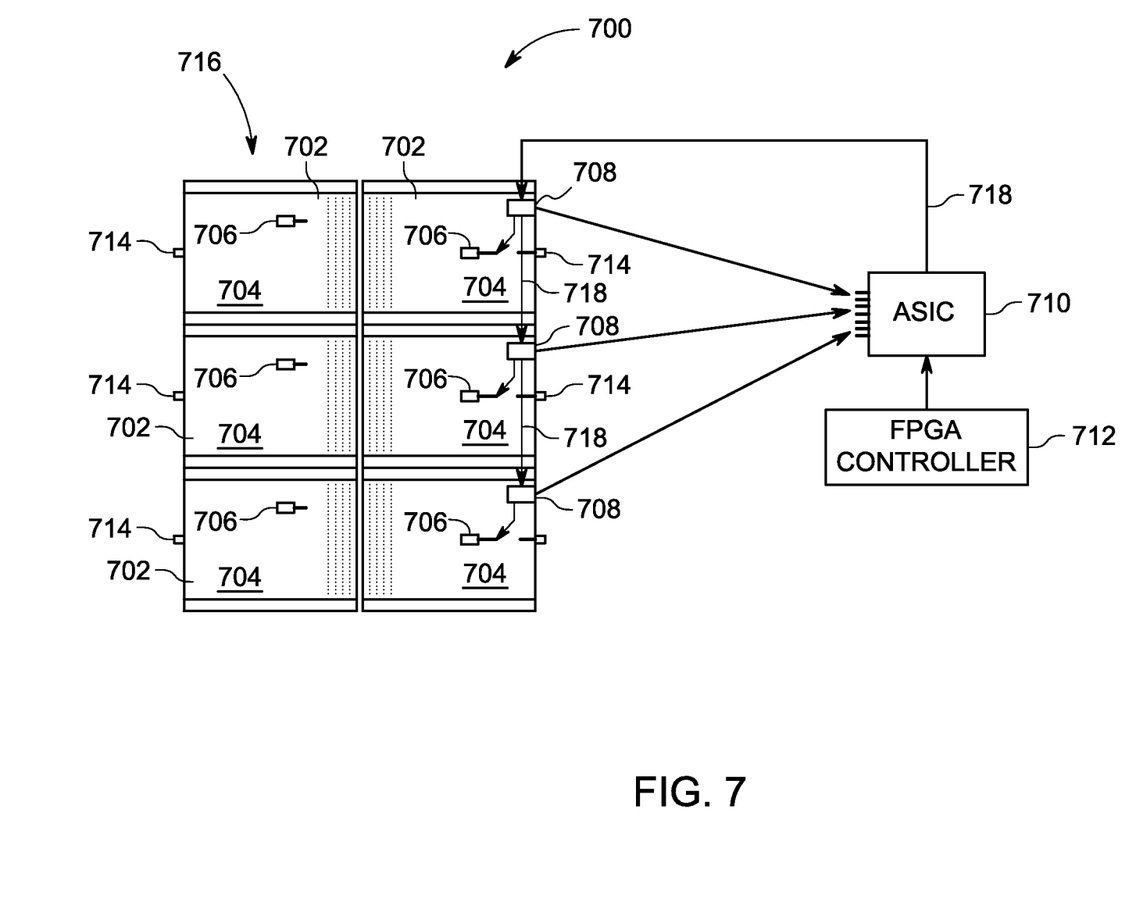
FIG. 7 illustrates a block diagram of SiPMs having areas for gain determination, and multiplexers (or switches) and located as part of the SiPMs.

According to another example, FIG. 7 illustrates a detector 700 having SiPMs 702 that include arrays 704 of microcells that are APDs operated in Geiger mode. Each SiPM 702 includes an area 706 of one or more microcells electrically isolated from all others of arrays 704. Areas 706 include multiplexers 708 that are coupled directly to an ASIC 710, which is coupled to an ASIC controller 712. In contrast to the previous examples, high-gain amplifier and digitization occurs within ASIC 710. Multiplexers 708 are positioned as part of their respective SiPM 702, and switchably coupled between 1) each area 706, and 2) anodes 714 that are common to all other microcells of respective arrays 704. ASIC 710 is configured to switchably operate multiplexers 708 to determine the gain of each SiPM 702 from the respective area 706.

Anode outputs 714 are common anodes to each respective array 704 of microcells, and each anode output 714 is electrically coupled to ASIC 710 (and SiPMs 716 are also coupled to ASIC 710, though not shown, but may be coupled to another ASIC, in another example). Thus, FIG. 7 illustrates an example wherein multiplexers 708 are positioned as part of each SiPM 702, and positioned to receive signals from areas 706 to determine the gain of the respective SiPM 702. Control to ASIC 710 and between multiplexers 708 is via a multiplexing control signal 718. Thus, multiplexing and switching can be implemented directly on the SiPM device. In one example, a high gain amplifier may be included and selectable when high gain amplifier is used to measure single photon signals.

In the examples of FIGS. 5-7, an area of the SiPM is dedicated to gain measurement that is relatively small so that dedication for SiPM gain determination has a minimal effect on the overall photon detection efficiency of the SiPM. An alternative solution is to select larger areas that can be used to measure gain and measure the actual signal as well. That is, while it may not be possible to measure signals from individually thermally produced electron-hole pairs from an anode of, for instance 27 mm$^2$, it is possible to measure them with, for instance an area of 9 mm$^2$.

Figure 8:
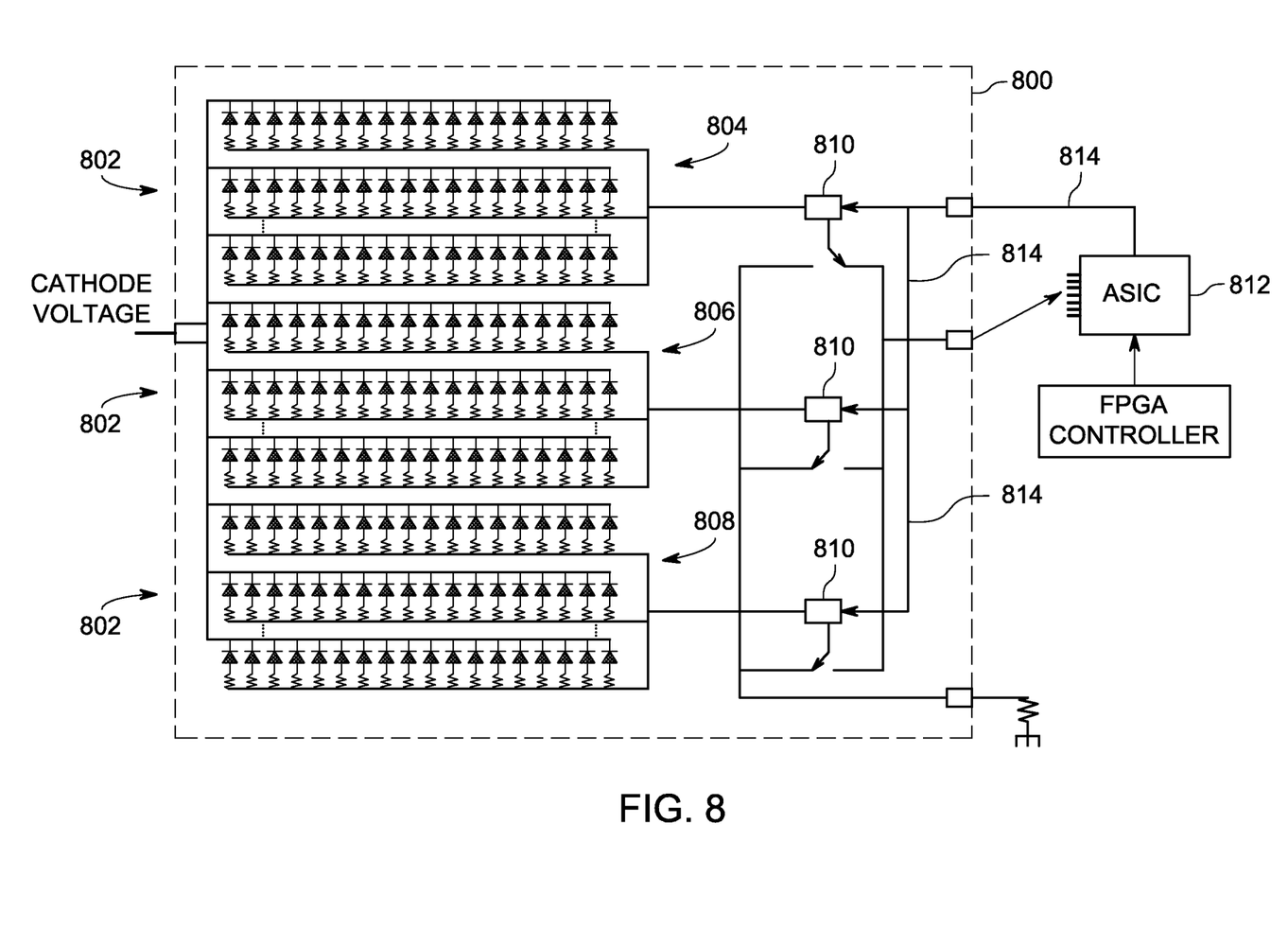
FIG. 8 illustrates a SiPM having separate anode areas that can be selectively engaged by a switching device that is located as part of the SiPM.

Thus, FIG. 8 illustrates an example in which SiPM 800 has, as an example, three regions 802 in a SiPM. And, although only one SiPM 800 is illustrated, it is contemplated that a plurality of SiPMs 800 may be implemented in a system, such as system 100. A first area 804 includes a first plurality of microcells, a second area 806 includes a second plurality of microcells, and a third area 808 includes a third plurality of microcells that are connected in a third group. Multiplexers or switches 810 are coupled to respective areas 804, 806, 808, and multiplexers 810 are switchably engageable to select one of the first, second, and third groups 804, 806, 808 such that the selected group is used to determine the gain of SiPM 800. An ASIC 812 operates a switch control line 814, and an AISC controller 816 is coupled to ASIC 812. When measuring the light signal (i.e., desired detector signal for imaging), all regions 804, 806, 808 are connected to ASIC 812, but for measuring the gain of SiPM 800, then only one of regions 804, 806, 808 is used. As such, in this example, it is possible to measure an average gain over each region 804, 806, 808, and the average gain for the entire anode of SiPM 800 is obtained. And, since gain measurement is performed with one or several photons, the high gain amplifier is selectable inside ASIC during the gain measurement. Examples in FIGS. 7 and 8 shares channels in an ASIC for gain calibration and anode signal readout, which indicates gain calibration and anode readout could not be done in parallel. Therefore this configuration is used when the temperature of a system is known to be stable during a patient scan and so, the calibration can be accomplished just before a patient scan.

According to one embodiment, an imaging system includes a first silicon photomultiplier (SiPM) comprising an array of microcells. Each microcell is an avalanche photodiode (APD) operated in a Geiger mode, a first area of the first SiPM, comprising at least one of the microcells, is electrically isolated from all other microcells, and a signal from the first area, resulting from at least one photon pulse, is used to determine a gain of the first SiPM.

According to another embodiment, a method of measuring a gain includes receiving a signal from a first area of a first silicon photomultiplier (SiPM), wherein the first area comprises at least one microcell that is part of but isolated from an array of microcells, and wherein each microcell in the array is an avalanche photodiode (APD), and measuring the gain of the first SiPM using the signal that results from at least one photon pulse that emanates from a scintillator that is coupled to the first SiPM.

According to yet another embodiment, a system for calibrating a detector includes a first silicon photomultiplier (SiPM) comprising a first array of microcells, each of which is an avalanche photodiode (APD) operated in a Geiger mode, a first area of the first array, comprising at least one of the microcells electrically isolated from all other microcells of the first array, a signal from the first area, resulting from at least one photon pulse, is used to determine a gain of the first SiPM, and a scintillator optically coupled to the first SiPM, wherein gamma rays emitted from a patient positioned in the imaging system pass to the scintillator and generate photons that pass to the first SiPM.

A technical contribution for the disclosed method and apparatus is that it provides for a computer-implemented apparatus and method to determine a gain of a detector.

When introducing elements of various embodiments of the disclosed materials, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the preceding discussion is generally provided in the context of medical imaging, it should be appreciated that the present techniques are not limited to such medical contexts. The provision of examples and explanations in such a medical context is to facilitate explanation by providing instances of implementations and applications. The disclosed approaches may also be utilized in other contexts, such as the non-destructive inspection of manufactured parts or goods (i.e., quality control or quality review applications), and/or the non-invasive inspection of packages, boxes, luggage, and so forth (i.e., security or screening applications).

While the disclosed materials have been described in detail in connection with only a limited number of embodiments, it should be readily understood that the embodiments are not limited to such disclosed embodiments. Rather, that disclosed can be modified to incorporate any number of variations, alterations, substitutions or equivalent arrangements not heretofore described, but which are commensurate with the spirit and scope of the disclosed materials. Furthermore, while single energy and dual-energy techniques are discussed above, that disclosed encompasses approaches with more than two energies. Additionally, while various embodiments have been described, it is to be understood that disclosed aspects may include only some of the described embodiments. Accordingly, that disclosed is not to be seen as limited by the foregoing description, but is only limited by the scope of the appended claims.

What is claimed is:

1. An imaging system comprising:
a first silicon photomultiplier (SiPM) comprising an array of microcells, wherein each microcell is an avalanche photodiode (APD) operated in a Geiger mode, a first area of the first SiPM, comprising at least one of the microcells, is electrically isolated from all other microcells, and a signal from the first area, resulting from at least one photon pulse, is used to determine a gain of the first SiPM; and
a first multiplexer disposed on the first SiPM and electrically coupled to the first area of the first SiPM that is electrically isolated from the array of microcells and is configured to receive the signal from the first area and pass the signal to a high gain amplifier.

2. The imaging system of claim 1, comprising a scintillator optically coupled to the first SiPM, wherein gamma rays emitted from a patient positioned in the imaging system pass to the scintillator and generate photons that pass to the first SiPM.

3. The imaging system of claim 1, further comprising a second SiPM positioned proximate the first SiPM, and comprising an application-specific integrated circuit (ASIC) electrically coupled to the first and second SiPMs, wherein imaging signals from the first and second SiPMs pass to the ASIC and are processed in the ASIC and converted to digitized imaging data in one or more of the ASIC or in an external digitizer.

4. The imaging system of claim 3, wherein the first multiplexer is positioned apart from the first and second SiPMs, and positioned to receive a second signal from a second area of the second SiPM to determine a gain of the second SiPM, and the ASIC is positioned apart from the first and second SiPMs.

5. The imaging system of claim 3, wherein the first multiplexer is positioned on the first SiPM, and positioned to receive the second signal from the second area of the second SiPM to determine the gain of the second SiPM, and the ASIC is positioned apart from the first and second SiPM.

6. The imaging system of claim 3, wherein the first multiplexer is positioned as part of the first SiPM and switchably coupled between 1) the first area, and 2) a first anode or cathode that is common to all other microcells of the first SiPM;

further comprising a second multiplexer positioned as part of the second SiPM and switchably coupled between 3) the second area of the second SiPM, and 4) a second anode or cathode that is common to all other microcells of the second SiPM;

wherein the ASIC is configured to switchably operate the first and second multiplexers to determine the gain of the first SiPM from the first area of the first SiPM, and to determine the gain of the second SiPM from the second area of the second SiPM.

7. The imaging system of claim 1, wherein the first area of the first SiPM comprises a first plurality of microcells that are connected in a first group, the first SiPM comprises a second plurality of microcells that are connected in a second group, and the first SiPM comprises a third plurality of microcells that are connected in a third group; further comprising a second multiplexer coupled to the second area and a third multiplexer coupled to the third area; wherein the first, second, and third multiplexers are switchably engageable to select one of the first, second, and third groups such that the selected group is used to determine the gain of the first SiPM.

8. A method of measuring a gain, comprising:
receiving a first signal at a first multiplexer disposed on a first silicon photomultiplier (SiPM) and electrically coupled with a first area of the first SiPM, the first signal received from the first area of the first SiPM, wherein the first area comprises at least one microcell that is part of but selectively isolated from an array of microcells, and wherein each microcell in the array is an avalanche photodiode (APD);
passing the first signal from the first multiplexer to a high gain amplifier; and
measuring the gain of the first SiPM using the first signal that results from at least one photon pulse that emanates from a scintillator that is coupled to the first SiPM.

9. The method of claim 8, further comprising:
receiving a second signal from a second area of a second SiPM; and
determining the gain of the second SiPM using the second signal.

10. The method of claim 9, further comprising receiving the second signal in the first multiplexer, wherein the first multiplexer is positioned apart from the first and second SiPMs.

11. The method of claim 9, further comprising receiving the second signal in the first multiplexer.

12. The method of claim 9, further comprising:
receiving the first signal in the first multiplexer;
receiving the second signal in a second multiplexer;
wherein the second multiplexer is positioned on the second SiPM.

13. The method of claim 8, wherein the first area of the first SiPM comprises a first plurality of microcells that are connected in a first group, the first SiPM comprises a second plurality of microcells that are connected in a second group, and the first SiPM comprises a third plurality of microcells that are connected in a third group;

wherein the respective multiplexers are switchably engageable to select one of the first, second, and third groups such that the selected group is used to determine the gain of the first SiPM.

14. A system for calibrating a detector, comprising:
a first silicon photomultiplier (SiPM) comprising a first array of microcells, each of which is an avalanche photodiode (APD) operated in a Geiger mode;
a first area of the first array, comprising at least one of the microcells electrically isolated from all other microcells of the first array;
a first multiplexer disposed on the first SiPM and electrically coupled to the first area of the first SiPM that is electrically isolated from the first array of microcells, the first multiplexer receiving a first signal from the first area, resulting from at least one photon pulse, and passing the first signal to an amplifier to determine a gain of the first SiPM; and
a scintillator optically coupled to the first SiPM, wherein gamma rays emitted from a body positioned in the imaging system pass to the scintillator and generate photons that pass to the first SiPM.

15. The system of claim 14, wherein the first multiplexer receives the first signal from the first area and selectively passes the first signal to the amplifier which includes a high gain amplifier.

16. The system of claim 15, comprising a second SiPM positioned proximate the first SiPM, and comprising an application-specific integrated circuit (ASIC) electrically coupled to the first and second SiPMs, wherein imaging signals from the first and second SiPMs pass to the ASIC and are converted to digitized imaging data in the ASIC.

17. The system of claim 16, wherein the first multiplexer is positioned apart from the first and second SiPMs, and positioned to receive a second signal from a second area of the second SiPM to determine a gain of the second SiPM, and the ASIC is positioned apart from the first and second SiPMs.

18. The system of claim 16, wherein the first multiplexer is positioned on the first SiPM, and positioned to receive a second signal from a second area of the second SiPM to determine a gain of the second SiPM, and the ASIC is positioned apart from the first and second SiPM.

19. The system of claim 16, wherein the first multiplexer is positioned as part of the first SiPM and switchably coupled between 1) the first area, and 2) a first anode or cathode that is common to all other microcells of the first SiPM;

further comprising a second multiplexer positioned as part of the second SiPM and switchably coupled between 3) the second area of the second SiPM, and 4) a second anode or cathode that is common to all other microcells of the second SiPM;

wherein the ASIC is configured to switchably operate the first and second multiplexers to determine the gain of the first SiPM from the first area of the first SiPM, and to determine the gain of the second SiPM from the second area of the second SiPM.

* * * * *